(12) United States Patent
Rosen et al.

(10) Patent No.: US 7,825,094 B2
(45) Date of Patent: Nov. 2, 2010

(54) METHOD OF TREATMENT FOR CANCERS ASSOCIATED WITH ELEVATED HER 2 LEVELS

(75) Inventors: Neal Rosen, Englewood, NJ (US); Pamela Munster, Tampa, FL (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 1594 days.

(21) Appl. No.: 10/478,023

(22) PCT Filed: May 23, 2002

(86) PCT No.: PCT/US02/16287

§ 371 (c)(1),
(2), (4) Date: Mar. 29, 2004

(87) PCT Pub. No.: WO02/094196

PCT Pub. Date: Nov. 28, 2002

(65) Prior Publication Data

US 2004/0266746 A1    Dec. 30, 2004

Related U.S. Application Data

(60) Provisional application No. 60/293,246, filed on May 23, 2001.

(51) Int. Cl.
 *C12Q 1/68* (2006.01)
(52) U.S. Cl. ............................................. 514/25; 435/6
(58) Field of Classification Search ........................ None
See application file for complete search history.

(56) References Cited

U.S. PATENT DOCUMENTS

| | | | |
|---|---|---|---|
| 4,261,989 A | 4/1981 | Sasaki et al. |
| 5,387,584 A | 2/1995 | Schnur |
| 5,650,430 A | 7/1997 | Sugimura et al. |
| 5,932,566 A | 8/1999 | Schnur et al. |
| 5,968,921 A | 10/1999 | Gold |
| 6,210,974 B1 | 4/2001 | Gold |
| 6,239,168 B1 | 5/2001 | Ino et al. |
| 6,335,157 B1 | 1/2002 | Gonzalez et al. |
| 6,413,975 B1 | 7/2002 | Chasin et al. |
| 6,440,982 B1 | 8/2002 | Maw et al. |

FOREIGN PATENT DOCUMENTS

| WO | WO 96/32480 | 10/1996 |
|---|---|---|
| WO | WO 96/40789 | 12/1996 |
| WO | WO 97/04801 | 2/1997 |
| WO | WO 98/51702 | 11/1998 |
| WO | WO 00/61578 | 10/2000 |

OTHER PUBLICATIONS

Workman, P. Auditing the Pharmacological Accounts for Hsp90 Molecular Chaperone Inhibitors: Unfolding the Relationship between Pharmacokinetics and Pharmacodynamics, Molecular Cancer Therapeutics 2:131-138, 2003.*

Wu, T. Analysing Gene Expression Data from DNA Microarrays to Identify Candidate Genes, J. Pathol. 195(1):53-65, 2001.*

Lucitini, J. Gene Association Studies Typically Wrong, The Scientist 18(24):20, 2004.*

Chen, G. et al. Discordant Protein and mRNA Epxression in Lung Adenocarcinomas, Molecular and Cellular Proteomics 1:304-313, 2002.*

Isaacs, J. et al. Heat Shock Protein 90 as a Molecular Target for Cancer Therapeutics, Cancer Cell 3:213-217, 2003.*

Roe, S.M. et al. Structural Basis for Inhibition of the Hsp90 Molecular Chaperone by the Antitumor Antibiotics Radicicol and Geldanamycin, J. Med. Chem. 42:260-266, 1999.*

Chiosis, G. et al. A Small Molecule Designed to Bind to the Adenine Nucleotide Pocket of Hsp90 Causes Her2 Degradation and the Growth Arrest and Differentiation of Breast Cancer Cells, Chemistry & Biology 8:289-299, 2001.*

Tommasi et al. (1992) Tumori 78:106-110.*

Kelland et al. (1999) J. Natl. Cancer Inst. 91:1940-1949.*

Mandler et al. (2000) J. Natl. Cancer Inst. 92:1573-1581.*

Tokuda et al. (1999) Br. J. Cancer 81:1419-1425.*

Münster et al. (2002) Cancer Res. 62:3132-3137.*

Bamberger et al., Inhibition of mineralocorticoid and glucocorticoid receptor function by the heat shock protein 90-binding agent geldanamycin, Molecular and Cellular Endocrinology, 1997, pp. 233-240, vol. 131, No. 2.

Black et al., Reactions of Ninhydrin with Activated Anilines: Formation of Indole Derivatives, 1994, pp. 10983-10994, vol. 50, No. 37, See Compound 17.

Bohen, Genetic and Biochemical Analysis of p23 and Ansamycin Antibiotics in the Function of HSP9O-Dependent Signaling Proteins, Molecular and Cellular Biology, 1998, pp. 3330-3339, vol. 18, No. 6.

Chavany et al., p185$^{erbB2}$ Binds to GRP94 in Vivo, Journal of Biological Chemistry, 1996, pp. 4974-4977, vol. 271, No. 9.

Chen et al., The Ah Receptor is a Sensitive Target of Geldanamycin-Induced Protein Turnover, Archives of Biochemistry and Biophysics, 1997, pp. 190-198, vol. 348, No. 1.

Kato et al., Synthesis of Compounds related to Antitumor Agents. IV. On The Reaction of Aromatic Carboxylates with 2,4 Diamino-5-hydroxy-6-methylpyrimidine, 1976, pp. 2461-2469, , vol. 24, No. 10, Publisher: See Table 2.

Landel et al., Estrogen Receptor Accessory Proteins Augment Receptor—DNA Interaction and DNA Bending, The Journal of Steroid Biochemistry & Molecular Biology, 1997, pp. 59-73, vol. 63, No. 1-3.

Munster et al., Inhibition of Heat Shock Protein 90 Function by Ansamycins Causes the Morphological and Functional Differentiation of Breast Cancer Cells, Cancer Research, 2001, pp. 2945-2952, vol. 61.

(Continued)

*Primary Examiner*—James S Ketter
(74) *Attorney, Agent, or Firm*—Larson & Anderson, LLC

(57) ABSTRACT

Novel methods of treating proliferative disorders characterized by elevated Her-2, and the patient is then administered an effective amount of an HSP90 inhibitor.

29 Claims, 5 Drawing Sheets

OTHER PUBLICATIONS

Neckers, L., Effects of Geldanamycin and Other Naturally Occurring Small Molecule Antagonists of Heat Shock Protein 90 on HER2 Protein Expression, Breast Disease, 2000, vol. 11, pp. 49-59.

Pratt, The hsp90-based Chaperone System: Involvement in Signal Transduction from a Variety of Hormone and Growth Factor Receptors, Proceedings of the Society for Experimental Biology and Medicine, 1998, pp. 420-434, vol. 217, No. 4.

Rosenhagen et al., Synergistic Inhibition of the Glucocorticoid Receptor by Radicicol and Benzoquinone Ansamycins, Biol. Chem., 2001, pp. 499-504, vol. 382.

Scheibel et al., Two chaperone sites in Hsp90 differing in substrate specificity and ATP dependence, Proceedings of the National Academy of Sciences, , pp. 1495-1499, vol. 95, No. 4.

Schnur et al., erbB-2 Oncogene Inhibition by Geldanaymycin Derivatives: Synthesis, Mechanism of Action, and Structure—Activity Relationships, J. Med. Chem., 1995, pp. 3813-3820, vol. 38.

Schulte et al., The benezoquinone ansamycin 17-allylamino-17-demethoxygeldanamycin binds to HSP90 and shares important biologic activities with geldanamycin, Cancer Chemotherapy and Pharmacology, 1998, pp. 273-279, vol. 42.

Segnitz et al., The Function of Steroid Hormone Receptors Is Inhibited by the hsp90-specific Compound Geldanamycin, The Journal of Biological Chemistry, 1997, pp. 18694-18701, vol. 272, No. 30.

Stebbins et al., Crystal Structure of an Hsp9O-Geldanamycin Complex:: Targeting of a Protein Chaperone by an Antitumor Agent, Molecular Biology, 1997, pp. 239-250, vol. 89.

Stockwell et al., High-throughput screening of small molecules in miniaturized mammalian cell-based assays involving post-translational modifications, Chemistry and Biology, 1999, pp. 71-83, vol. 6.

Zheng F F et al., "Identification of a geldanamycin dimer that induces the selective degradation of HER-family tyrosine kinases." Cancer Research. Apr. 15, 2000, pp. 2090-2094, vol. 60, No. 8.

Hartmann F et al., "Effects of the tyrosine-kinase inhibitor geldanamycin on ligand-induced Her-2/neu activation, receptor expression and proliferation of Her-2-positive malignant cell lines." International Journal of Cancer. Jan. 17, 1997, pp. 221-229, vol. 70 No. 2.

An W G et al., "Depletion of P185ERBB2, RAF-1 and Mutant P53 Proteins by Geldanamycin Derivatives Correlates with Antiproliferative Activity." Cancer Chemotherapy and Pharmacology, Springer Verlag. 1997, pp. 60-64, vol. 40, No. 1.

Supko J G et al., "Preclinical pharmacologic evaluation of geldanamycin as an antitumor agent." Cancer Chemotherapy and Pharmacology. 1995, pp. 305-315, vol. 36, No. 4.

Schnur et al., "Inhibition of the Oncogene Product p185erb-b2 in Vitro and in Vivo by Geldanamycin and Dihydrogeldanamycin Derivatives." Journal of Medicinal Chemistry, American Chemical Society. 1995. pp. 3806-3812, vol. 38, No. 19.

Smith D F et al., "Molecular chaperones, Biology and prospects for pharmacological intervention." Pharamcological Reveiws. 1998. pp. 493-513, vol. 50, No. 4.

Smith V et al., "The effect of overexpression of C-ERBB2 on the chemosensitivity of a human ovarian carcinoma cell line." British Journal of Cancer. 2001. p. 100, #P263, vol. 85, No. Supplement 1 XP008064337.

* cited by examiner

METHOD OF TREATMENT FOR CANCERS ASSOCIATED WITH ELEVATED HER 2 LEVELS

This application is a 371 national stage of PCT/US02/16287, filed May 23, 2002, and claims the benefit of U.S. Provisional Application No. 60/293,246, filed May 23, 2001.

FIELD OF THE INVENTION

The field of the invention relates to chemotherapeutic treatment of cancers.

BACKGROUND OF THE INVENTION

The following description includes information that may be useful in understanding the present invention. It is not an admission that any of the information provided herein is prior art, or relevant, to the presently claimed inventions, or that any publication specifically or implicitly referenced is prior art.

The eukaryotic heat shock protein 90s (HSP90s) are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J., 1999, *TIBS*, 24:136-141; Stepanova, L. et al., 1996, *Genes Dev.* 10: 1491-502; Dai, K. et al., 1996, *J. Biol. Chem.* 271:22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see, e.g., Caplan, A., 1999, *Trends in Cell Biol.*, 9: 262-68).

Ansamycin antibiotics derived from *Streptomyces hygroscopicus* are known to inhibit HSP90s. These antibiotics, e.g., herbimycin A (HA) and geldanamycin (GM), as well as other HSP90 inhibitors such as radicicol, bind tightly to an N-terminus pocket in HSP90 (Stebbins, C. et al., 1997, *Cell*, 89:239-250). This pocket is highly conserved and has weak homology to the ATP-binding site of DNA gyrase (Stebbins, C. et al., supra; Grenert, J. P. et al., 1997, *J. Biol. Chem.*, 272:23843-50). Further, ATP and ADP have both been shown to bind this pocket with low affinity and to have weak ATPase activity (Proromou, C. et al., 1997, *Cell*, 90: 65-75; Panaretou, B. et al., 1998, *EMBO J.*, 17: 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T., H. et al., 1999, *Proc. Natl. Acad. Sci. USA* 96:1297-302; Schulte, T. W. et al., 1995, *J. Biol. Chem.* 270: 24585-8; Whitesell, L., et al., 1994, *Proc. Natl. Acad. Sci. USA* 91:8324-8328). Ansamycins have also been demonstrated to inhibit the ATP-dependent release of chaperone-associated protein substrates (Schneider, C., L. et al., 1996, *Proc. Natl. Acad. Sci. USA*, 93:14536-41; Sepp-Lorenzino et al., 1995, *J. Biol. Chem.* 270:16580-16587). In either event, the substrates are degraded by a ubiquitin-dependent process in the proteasome (Schneider, C., L., supra; Sepp-Lorenzino, L., et al., 1995, *J. Biol. Chem.*, 270:16580-16587; Whitesell, L. et al., 1994, *Proc. Natl. Acad. Sci. USA*, 91: 8324-8328).

This substrate destabilization occurs in tumor and non-transformed cells alike and has been shown to be especially effective on a subset of signaling regulators, e.g., Raf (Schulte, T. W. et al., 1997, *Biochem. Biophys. Res. Commun.* 239:655-9; Schulte, T. W., et al., 1995, *J. Biol. Chem.* 270:24585-8), nuclear steroid receptors (Segnitz, B., and U. Gehring. 1997, *J. Biol. Chem.* 272:18694-18701; Smith, D. F. et al., 1995, *Mol. Cell. Biol.* 15:6804-12), v-src (Whitesell, L., et al., 1994, *Proc. Natl. Acad. Sci. USA* 91:8324-8328) and certain transmembrane tyrosine kinases (Sepp-Lorenzino, L. et al., 1995, *J. Biol. Chem.* 270:16580-16587) such as EGF receptor (EGFR) and Her2/Neu (Hartmann, F., et al., 1997, *Int. J. Cancer* 70:221-9; Miller, P. et al., 1994, *Cancer Res.* 54:2724-2730; Mimnaugh, E. G., et al., 1996, *J. Biol. Chem.* 271:22796-801; Schnur, R. et al., 1995, *J. Med. Chem.* 38:3806-3812). The ansamycin-induced loss of these proteins leads to the selective disruption of certain regulatory pathways and results in growth arrest at specific phases of the cell cycle (Muise-Heimericks, R. C. et al., 1998, *J. Biol. Chem.* 273:29864-72), and apoptsosis, and/or differentiation of cells so treated (Vasilevskaya, A. et al., 1999, *Cancer Res.*, 59:3935-40).

Growth arrest of this sort, provided it can be made selective, has important ramifications for the treatment of proliferative diseases, i.e., cancers. Whereas cancer treatments have thus far been limited to traditional surgical removal, radiation, and/or chemotherapy, and whereas these procedures have been more or less successful, a need remains to develop additional therapies with increased efficacy and decreased side-effects. There particularly remains a need for cancer treatments that target specific cancer types, e.g., those characterized by the overexpression of Her-2/neu.

The Her-2/neu oncogene, also called erbB2, encodes a glycoprotein with tyrosine kinase activity known as p185 (Schechter, A. L. et al., 1984, *Nature*, 312: 513-516). HER-2 is a member of the epidermal growth factor receptor (EGFR) family and shares partial homology with other family members. In normal adult tissues, HER-2 expression is low; however, HER-2 is reported to be overexpressed in many tumors, including a significant fraction of human tumors of the breast, lung, ovary, and pancreas (Hynes, N. E. and Stem, D. F., 1994, *Biochem. Biophys. Acta.*, 1198: 165-184.) Studies indicate that HER-2 is overexpressed in at least 25-30% of breast cancers (McGuire & Greene, 1989, *Semin. Oncol.* 16: 148-155). Furthermore, overexpression of HER-2 in malignant breast tumors is correlated with increased metastasis, chemoresistance and poor survival rates (Slamon et al., 1987 *Science* 235: 177-182).

Because HER-2 overexpression is associated with and contributes to many types of mammalian proliferative diseases, a means of controlling such overexpression is much needed. A treatment that could simultaneously avoid or minimize harm to normal cells and tissues would be most desirable. The present invention satisfies these needs and provides related advantages as well.

SUMMARY OF THE INVENTION

Applicants have discovered that the sensitivity of cells typical of various proliferative disorders to the ansamycin CNF-101 ("17-AAG") is proportional to the HER-2 levels in those cells. This finding is counterintuitive because the vast majority of chemotherapeutic drugs that target oncogenic proteins display the exact opposite relationship with respect to their target proteins usually, elevated levels of oncogenic target proteins are associated with acquired or innate resistance to a given drug; the more protein, the less sensitivity. See, e.g., Inaba, M., 1997, *Nippon Rinsho* 55: 1030-1037; Mcleod H et al, 1996, *Brit. J Cancer* 74:508-512; Kinsella, A et al, 1998, *Gen. Pharmacol.* 30:623-626; Inaba, M., supra; Murakami, Y et al, 2000, *Int. J. Oncol.* 17:277-283.

In particular, the invention relates to methods of treating patients with cell proliferative disorders, including cancers, that are associated with elevated levels of HER-2 expression. The methods involve testing to determine an elevated level of HER-2, and administering a therapeutically effective amount of a HSP90 inhibitor. In preferred embodiments, the particular disorder is a cancer, particularly a breast cancer.

Accordingly, in a first aspect the method includes providing cells, tissue, or fluid from a patient suspected of having a proliferative disorder, testing the cells, tissue, or fluid for one or more of the gene copy number of HER-2, the amount of HER-2 mRNA, or the amount of HER-2 protein. If the level of HER-2 is elevated relative to normal cells, the method further includes administering to the patient a pharmaceutically effective amount of an HSP90 inhibitor.

The inhibitor may be an ansamycin or other type of small molecule HSP90 inhibitor, e.g., radicicol, or an analog thereof (see, e.g., U.S. Pat. Nos. 5,977,165, 5,650,430, and 5,597, 846). These compounds may be synthetic or natural. Preferred inhibitors include geldanamycin, 17-AAG, herbimycin A, and macbecin. The inhibitor preferably binds the ATP-binding site of a HSP90 and has an $IC_{50}$ that is lower, preferably at least two-fold lower, more preferably at least five-fold lower, and most preferably at least ten-fold lower for cancerous cells than for noncancerous cells. The inhibitor preferably exhibits an $IC_{50}$ of about 100 nM or less. Other embodiments feature 75 nM or less, 50 nM or less, 25 nM or less, 10 nM or less, and 5 nM or less. In preferred embodiments, the inhibitor is 17-AAG.

In the testing step, preferred embodiments include using nucleic acid hybridization or PCR to determine HER-2 gene copy number or the level of HER-2 messenger RNA. Additionally or alternatively, one may test for the presence of the HER-2 protein using, e.g., any of a variety of antibody-based techniques well known in the art. Testing may be done in vivo or in vitro (ex vivo), the latter, e.g., by biopsying cells.

Administration of HSP90 inhibitors may be done ex vivo or directly to the patient, e.g., parenterally, peripherally, or intralesionally. Testing may also be performed to measure the sensitivity of the patient's cells to one or more HSP90 inhibitors prior to administration of a particular HSP90 inhibitor as a therapeutic. This testing may be done on abnormal cells and/or normal cells alike to determine appropriate therapeutic amounts for administration. Positive and/or negative standards may be used in the testing step(s) to determine HER-2 levels and/or to evaluate inhibitor compound sensitivity.

In some embodiments, the methods of the invention may also include one or more testing steps following HSP90 inhibitor administration in order to monitor therapeutic effect. This step may include measuring a molecular marker that is indicative of the level of HER-2, e.g., HER-2 mRNA, a cyclin, and/or the level of phosphorylated AKT. Cyclins are preferably selected from the group consisting of D1 and D3, as those species are known in the art. Standards may also be used in this step.

An advantage of the invention is the ability to selectively target proliferative disorders that are characterized by cells exhibiting elevated HER-2 levels by administering an amount of HSP90 inhibitor that is effective against these particular cells, but that is relatively ineffective against normal cells. Other advantages will be apparent from the figures, the detailed specification, and the claims to follow.

Specifically, in one aspect of the invention there is provided a method of treating a patient having breast cancer characterized by breast cancer cells that have elevated levels of HER-2 expression as compared to non-cancerous cells of the same type. The method comprises the steps of (a) providing breast cancer cells from said patient;

(b) testing said provided cells for one or more of the gene copy number of HER-2, the amount of HER-2 mRNA, or the amount of HER-2 protein as an indication of the level of HER-2 expression; and if said level of HER-2 expression is elevated as compared to non-cancerous cells of the same type, (c) administering to said patient a pharmaceutically effective amount of an HSP90 inhibitor, wherein said inhibitor consists essentially of an ansamycin that binds into the ATP-binding site of a HSP90. The HSP90 inhibitor has an $IC_{50}$ at least two-fold lower for said provided cells in said patient having elevated Her-2 than for cells that do not have elevated Her-2 and the administered amount is correspondingly lower than the amount that would be required for cells that do not have elevated Her-2. The method further comprises the step of (d) testing to monitor therapeutic effect after said administration by measuring a molecular marker indicative of the level of HER-2.

In some embodiments of this method, the molecular marker is selected from one or more of the group consisting of a cyclin, and phosphorylated AKT.

DETAILED DESCRIPTION OF THE INVENTION

Definitions

Figure 1:
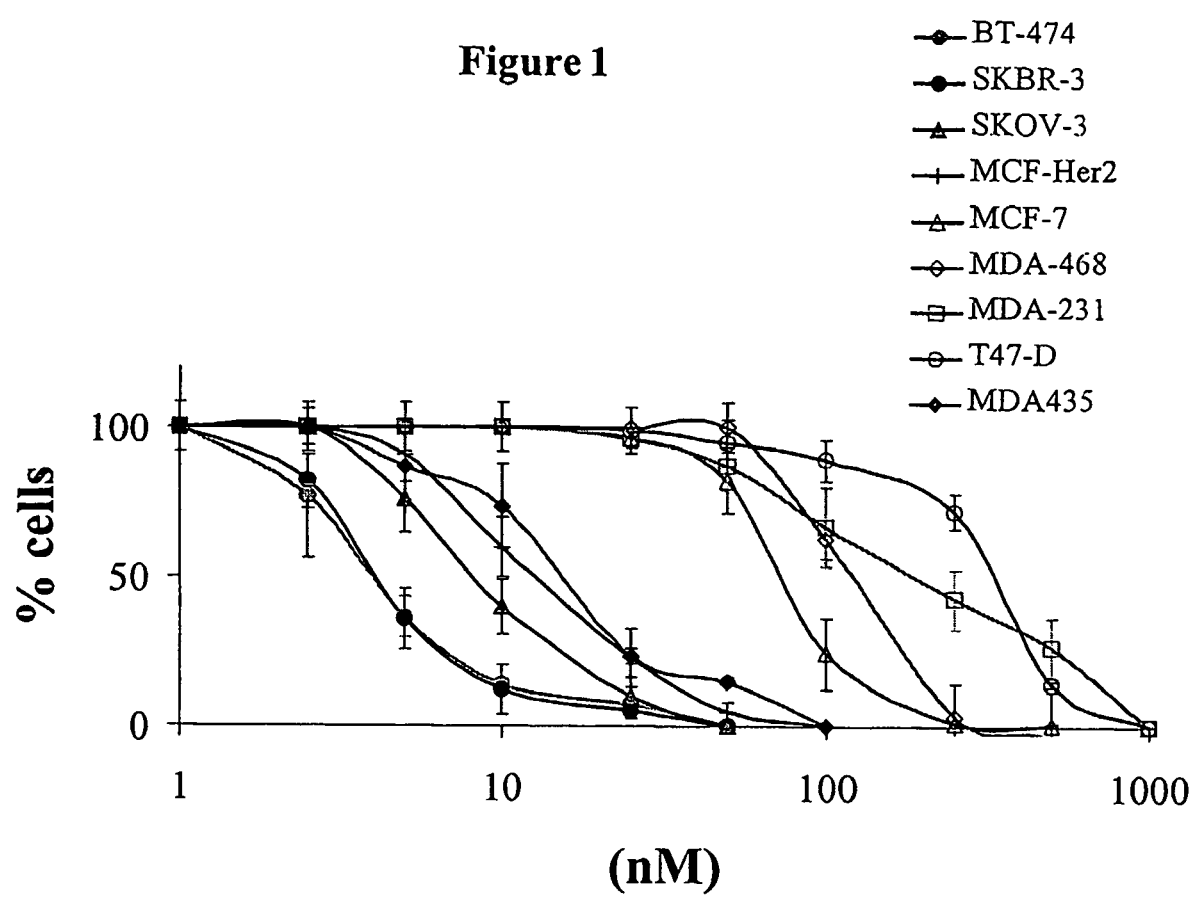
FIG. 1 shows the antiproliferative effect of CNF-101 (17-AAG) (17-AAG) on a panel of human breast cancer cells in vitro.

As used herein, the following terms have the following meanings.

By "elevated levels of HER-2 expression" is meant that more HER-2 protein is present relative to normal cells. This may be a consequence of gene amplification (multiple gene copy), enhanced transcription and/or translation from existing HER-2 genes and mRNA, and/or increased post-translational stability. By "elevated HER-2" is meant one or more of elevated HER-2 gene copy, mRNA transcript, or protein.

An "HSP90-inhibiting compound" or "HSP90-inhibitor" is one that disrupts the structure and/or function of an HSP90 chaperone protein and/or a protein that is dependent on HSP90. HSP90 proteins are highly conserved in nature (see, e.g., NCBI accession #'s P07900 and XM 004515 (human α and β HSP90, respectively), P11499 (mouse), AAB2369 (rat), P46633 (chinese hamster), JC1468 (chicken), AAF69019 (flesh fly), AAC21566 (zebrafish), AAD30275 (salmon), 002075 (pig), NP 015084 (yeast), and CAC29071 (frog). Grp94 and Trap-1 are related molecules falling within the definition of an HSP90-as used herein. There are thus many different HSP90s, all with anticipated similar effect and inhibition capabilities. The HSP90 inhibitors of the invention may be specifically directed against an HSP90 of the specific host patient or may be identified based on reactivity against an HSP90 homolog from a different species, or an HSP90 variant. The inhibitors used may be ring-structured antibiotics, e.g., benzoquinone ansamycins, or other types of molecules, e.g., antisense nucleic acids, or molecules such as radicicol and analogs thereof.

An "ansamycin" includes but is not limited to geldanamycin, 17-AAG, herbimycin A, and macbecin. The specific ansamycin 17-AAG stands for 17-allylamino-17-demethoxygeldanamycin. These and other ansamycins that can be used are well-known in the art. See, e.g., U.S. Pat. Nos. 3,595,955, 4,261,989, 5,387,584, and 5,932,566. Ansamycins may be synthetic, naturally-occurring, or else derivatives of naturally occurring ansamycins that are prepared using standard chemical derivatization techniques.

A "pharmaceutically effective amount" means an amount which is capable of providing a therapeutic or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 100 and more preferably 50 mg/kg of body weight of an active compound of this invention. Preferred daily doses generally will be from about 0.05 mg/kg to about 20 mg/kg and ideally from about 0.1 mg/kg to about 10 mg/kg.

The preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

The term "$IC_{50}$" is defined as the concentration of an HSP90 inhibitor required to achieve killing of 50% of the cells of a population, or of a particular cell type, e.g., cancerous versus noncancerous cells within a greater cell population. The $IC_{50}$ is preferably, although not necessarily, greater for normal cells than for cells exhibiting a proliferative disorder.

By a "standard" is meant a positive or negative control. A negative control in the context of HER-2 expression levels is, e.g., a sample possessing an amount of HER-2 (gene, transcript, and/or corresponding protein product) that correlates with a normal cell. A negative control may also include a sample that contains no HER-2 gene or gene-product, e.g., mRNA or protein. By contrast, a positive control does contain a HER-2 gene or gene product, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cells with high as opposed to relatively low or normal Her-2 levels.

General

The present invention concerns methods for treating cell proliferative disorders associated with high HER-2 levels based on the observation that cells which overexpress HER-2 are more sensitive to HSP90 inhibitors than cells which do not overexpress HER-2, e.g., normal cells. In any event, for diagnosis prior to treatment, and in embodiments where post-treatment evaluation is made, HER-2 levels may be determined.

Determining HER-2 Levels

Many different types of methods are known in the art for determining protein concentrations and measuring or predicting the level of proteins within cells and in fluid samples. Indirect techniques include nucleic acid hybridization and amplification using, e.g., polymerase chain reaction (PCR). These techniques are known to the person of skill and are discussed, e.g., in Sambrook, Fritsch & Maniatis, Molecular Cloning: A Laboratory Manual, Second Edition (1989) Cold Spring Harbor Laboratory Press, Cold Spring Harbor, N.Y., Ausubel, et al., Current Protocols in Molecular Biology, John Wiley & Sons, NY, 1994, and, as specifically applied to the quantification, detection, and relative activity of Her-2/neu inpatient samples, e.g., in U.S. Pat. Nos. 4,699,877, 4,918, 162, 4,968,603, and 5,846,749. A brief discussion of two generic techniques that can be used follows.

a. Immunodetection

The determination of whether cells overexpress or contain elevated levels of HER-2 can be determined using techniques well known in the art, e.g., antibody techniques such as immunoblotting, radioimmunoassays, western blotting, immunoprecipitation, enzyme-linked immunosorbant assays (ELISA), and derivative techniques that make use of antibodies directed against HER-2. As an example, HER-2 expression in breast cancer cells can be determined with the use of an immunohistochemical assay, such as the Dako Hercep™ test (Dako Corp., Carpinteria, Calif.). The Hercep™ test is an antibody staining assay designed to detect HER-2 overexpression in tumor tissue specimens. This particular assay grades HER-2 expression into four levels: 0, 1, 2, and 3, with level 3 representing the highest level of HER-2 expression. Accurate quantitation can be enhanced by employing an Automated Cellular Imaging System (ACIS) as described, e.g., by Press, M, et al, 2000, *Modern Pathology* 13:225A.

Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

b Nucleic Acid Techniques i. PCR

HER-2 overexpression can also be determined at the nucleic acid level since there is a reported high correlation between overexpression of the HER-2 protein and amplification of the gene that codes for it. One way to test this is by using RT-PCR. The genomic and cDNA sequences for HER-2 are known. Specific DNA primers can be generated using standard, well-known techniques, and can then be used to amplify template already present in the cell. An example of this is described in Kurokawa, H et al, Cancer Res. 60: 5887-5894 (2000), (which describes a forward primer having sequence 5'-TCTGGACGTGCCAGTGTGAA-3' (SEQ ID NO. 1) and a reverse primer having sequence 5'-TGCTCCCT-GAGGACACATCA-3' (SEQ ID NO. 2)). PCR can be standardized such that quantitative differences are observed as between normal and abnormal cells, e.g., cancerous and non-cancerous cells. Well known methods employing, e.g., densitometry, can be used to quantitate and/or compare nucleic acid levels amplified using PCR.

ii. Hybridization-based Techniques

Similarly, fluorescent in situ hybridization (FISH) assays and other assays can be used, e.g., Northern and/or Southern blotting. These rely on nucleic acid hybridization between the HER-2 gene or mRNA and a corresponding nucleic acid probe that can be designed in the same or a similar way as for PCR primers, above. See, e.g., Mitchell M S, and Press M F., 1999, *Semin. Oncol., Suppl.* 12:108-16. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, Cancer Res. 60: 5887-5894 (2000) (describing a nucleic acid probe having sequence 5'-FAM -CA-GAAGGCCAAGTCCGCAGAAGCC-TAMRA-p-3' (SEQ ID NO. 3)). ACIS-based approaches as described above can be employed to make the assay more quantitative (de la Torre-Bueno, J, et al, 2000, *Modern Pathology* 13:221A).

EXAMPLE 1

Antiproliferative Effects of 17-AAG (CNF-101) on Cancer Cells Which Express Different Amounts of HER-2

Human cancer cell lines BT-474, SKBR-3, SKOV-3, MCF-Her2, MCF-7, MDA-468, MDA-231, T47-D, and MDA435 were obtained from the American Type Culture Collection ("ATCC;" Manassas, Va., USA). Cell lines were maintained in DMEM/F2/1 medium, supplemented with 5% fetal calf serum (BRL), 2 mM glutamine, and 50 U/ml each of penicillin and streptomycin, at 37° C. in 5% $CO_2$.

Cells were treated for 24 hours with CNF-101 (17-AAG) at concentrations of 1 to 1000 nM. Following treatment, the nuclei were stained with ethidium bromide and analyzed by flow cytometry. Nuclei were isolated for flow cytometry assays, stained with ethidium bromide and analyzed using a Becton Dickinson fluorescence-activated cell sorter. Statistical data was obtained using Multicycle program software.

As shown in FIG. 1, in the cell lines examined, CNF-101 (17-AAG) treatment caused growth arrest in all the cell lines tested. Those cell lines expressing the highest levels of HER-2 were the most sensitive to CNF-101 (17-AAG) (FIG. 1). FIG. 1 shows the antiproliferative effect of CNF-101 (17-AAG) on a panel of human breast cancer cells in vitro. The cell lines expressing high endogenous levels of HER-2 (BT-474, SKBR-3, SKOV-3, MDA435) are markedly more sensitive to CNF-101 (17-AAG) than are the low HER-2 lines (MDA-468, MDA-231, T47D). Furthermore, the 10-fold difference in sensitivity between two cells from a congenic pair (MCF-7 vs. MCF-7/HER-2) differing only in their HER-2 levels demonstrate that HER-2 is the critical factor, rather than other potential variations between the cell lines.

EXAMPLE 2

Changes in Protein Expression Induced by CNF-101 (17-AAG) in HER-2 Negative Cells and Cells Which Overexpress HER-2

Levels of mitotic cyclin expression, HER-2 expression, AKT expression and Raf1 expression in MCF-7 (HER-2 negative) or BT-474 (HER-2+++) cell lines treated with CNF-101 (17-AAG) were assessed using immunoblot analysis. Immunoblot analysis of lysates from cells treated with either 50 nM or 500 nM CNF-101 (17-AAG) were analyzed by Western blot using anti-cyclin D1, anti-cyclin D3, anti-cyclin cdk4, anti-AKT or anti-Raf1 antibodies. All antibodies were obtained from Santa Cruz Biotechnology (Santa Cruz, Calif., USA). Treated cells were harvested, washed with PBS and lysed in NP40 lysis buffer (50 mM Tris pH7.4, 1% NP40,150 mM NaCl, 40 mM NaF. 1 mM Na3VO4, 1 mM phenylmethylsulfonylfluoride, and 10 µg/ml each of leupeptin, aprotinin and soybean trypsin inhibitor) for 30 min on ice. Lysates were centrifuged at 15,000×g for 10 min and protein concentration determined by bicinchoninic acid protein assay (Pierce). Equal amounts of total protein were resolved by SDS-PAGE and transferred onto Immobilon PVDF membranes (Millipore) by electroblotting. Blots were blocked overnight in 5% nonfat milk in TBS-T (0.1% Tween-20 TBS, 10 mM Tris pH 7.4, 150 mM NaCl) at 4° C. and subsequently probed with either anti-HER-2, anti-cylin D1, anti-cyclin D3, anti cdk4, anti-AKT or anti-Raf1 antibodies. Following incubation with HRP-conjugated secondary antibodies, proteins were detected by chemiluminescence (Amersham).

Figure 2:
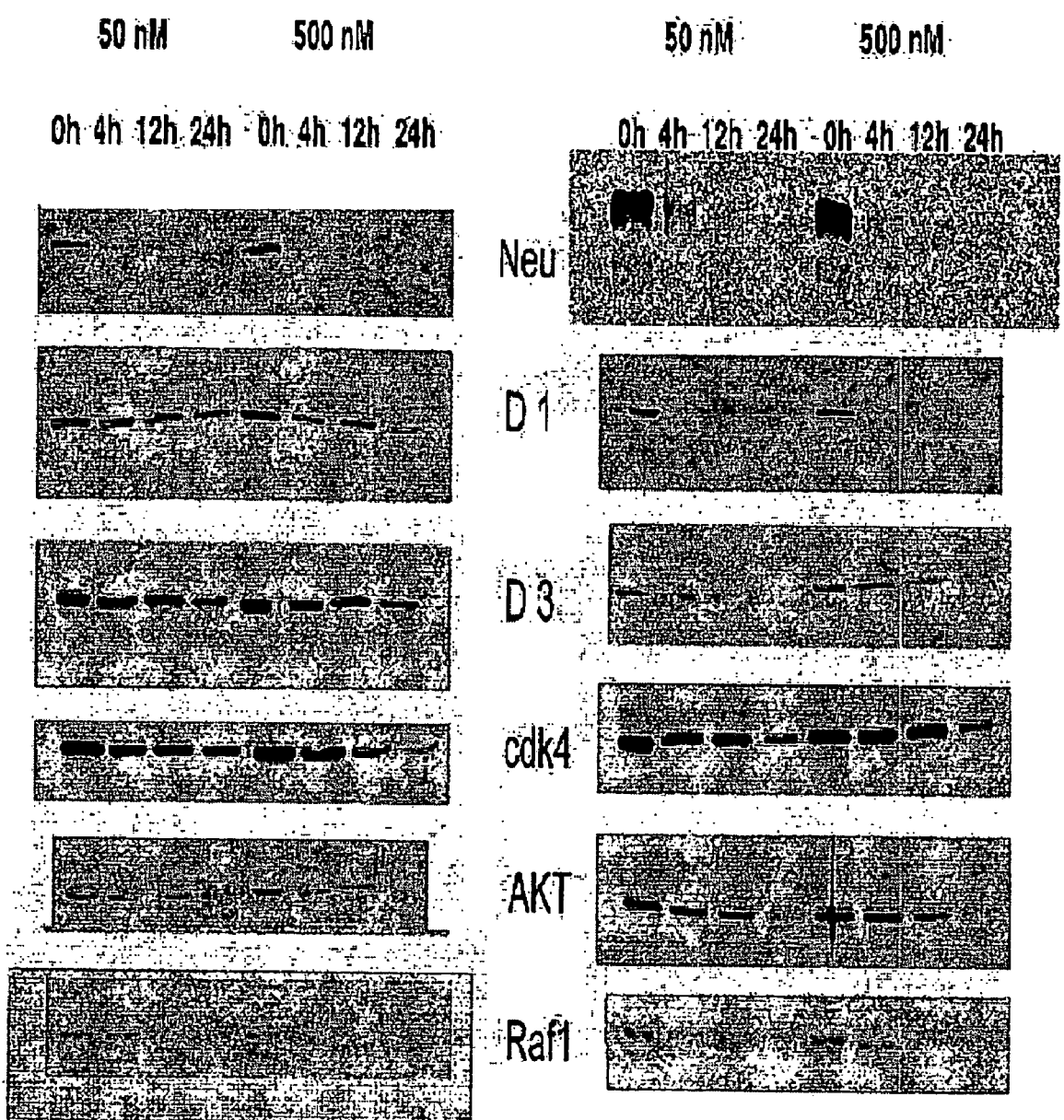
FIG. 2 shows the changes in levels of a HSP90 client protein (Raf-1) and of four downstream target proteins in HER-2+++ and HER-2-cells after treatment with CNF-101 (17-AAG) (17-AAG) in vitro.

FIG. 2 shows the changes in levels of HER-2 after treatment with CNF-101 (17-AAG) in vitro. Treatment of BT-474 cells (which over express HER-2) with 17-AAG resulted in the rapid decrease in cyclin D1 and cyclin D3 (FIG. 2). This decrease in cyclin D1 and D3 protein levels were not seen in MCF-7 cell lines (low HER-2 expression) (FIG. 2). The protein levels of cdk4, and AKT were not affected in either HER-2 overexpressing cells or HER low expressing cells after treatment with 17-AAG (FIG. 2). Cyclin D1 and cyclin D3 can be used according to the invention to indirectly monitor HER-2 expression and inhibitory effects thereon induced by HSP90 inhibitors.

EXAMPLE 3

Effect of CNF-101 (17-AAG) on AKT Expression, Phosphorylation and Activity

Figure 3:
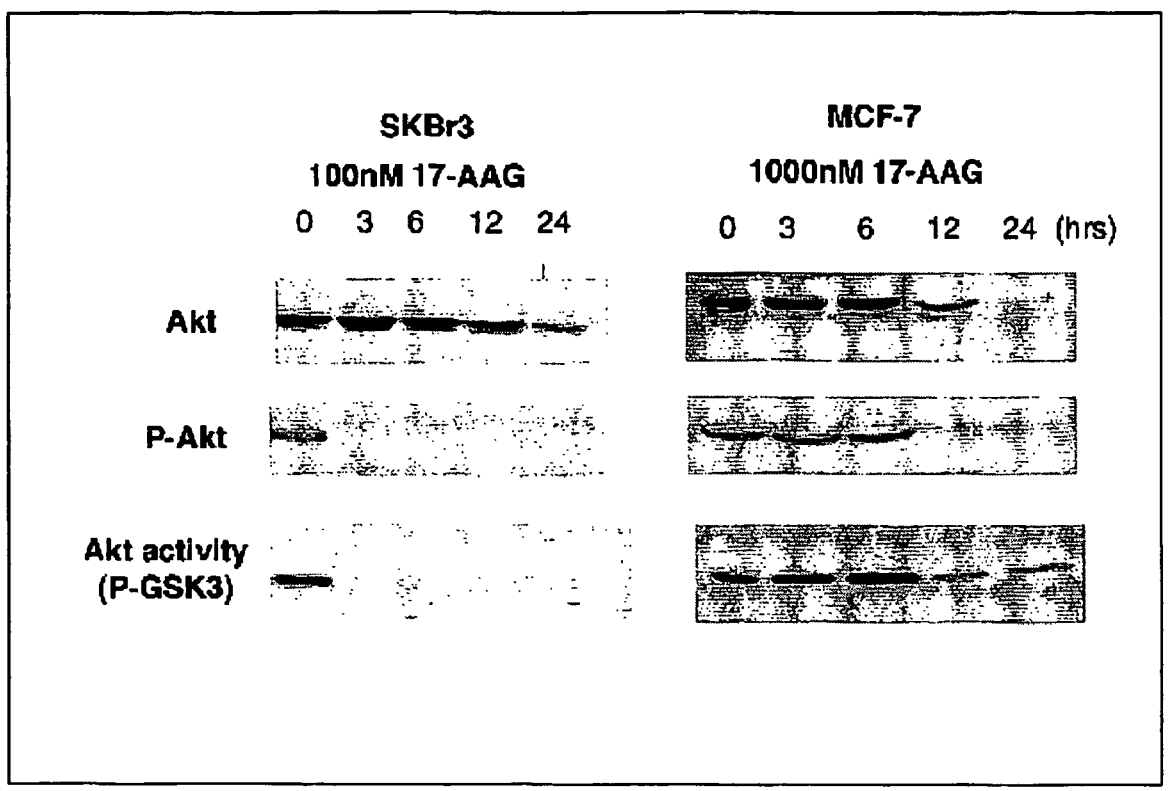
FIG. 3 shows the changes in protein levels, phosphorylation status, and kinase activity of AKT in HER-2+++ and HER-2-cells after treatment with CNF-101 (17-AAG) (17-AAG) in vitro.

FIG. 3 shows the changes in protein levels, phosphorylation status and kinase activity of AKT in HER-2+++ and HER-2-cells after treatment with CNF-101 (17-AAG) in vitro. Cells were treated with 1 uM CNF-101 (17-AAG) for 24 hrs, washed, harvested and lysed in NP-40. Lysates were resolved by SDS-PAGE, transferred onto Immobilon PVDF membranes, blocked in 5% nonfat milk and probed with antibodies to AKT or tyrosine phosphorylated AKT (phospho-AKT) from Upstate. Following incubation with HRP-conjugated secondary antibodies, proteins were detected using chemiluminescnce (Amersham). AKT kinase activity was assessed following immunoprecipitation by a standard kinase assay with the recombinant AKT substrate protein glycogen synthase kinase-1 (GSK-1) and 32-P labelled ATP. AKT is a key kinase in tumor cells. The protein itself is not a HSP90 client, so treatment with CNF-101 (17-AAG) does not cause significant loss of the protein. However, because the essential upstream regulator of the AKT pathway in breast cancer (i.e. HER-2) is degraded, the signals necessary for AKT phosphorylation (and hence activity of the protein) are lost, so phospho-AKT disappears from the treated cells. The experiment also shows a quantitative relationship between HER-2 levels and AKT inhibition: 100 nM CNF-101 (17-AAG) causes complete loss of AKT activity in high HER-2 (SKBr3) cells within 3 hrs, but even ten times that amount requires 12 hours to cause even partial loss of AKT kinase activity in the HER-2-low MCF-7 line.

EXAMPLE 4

Figure 4:
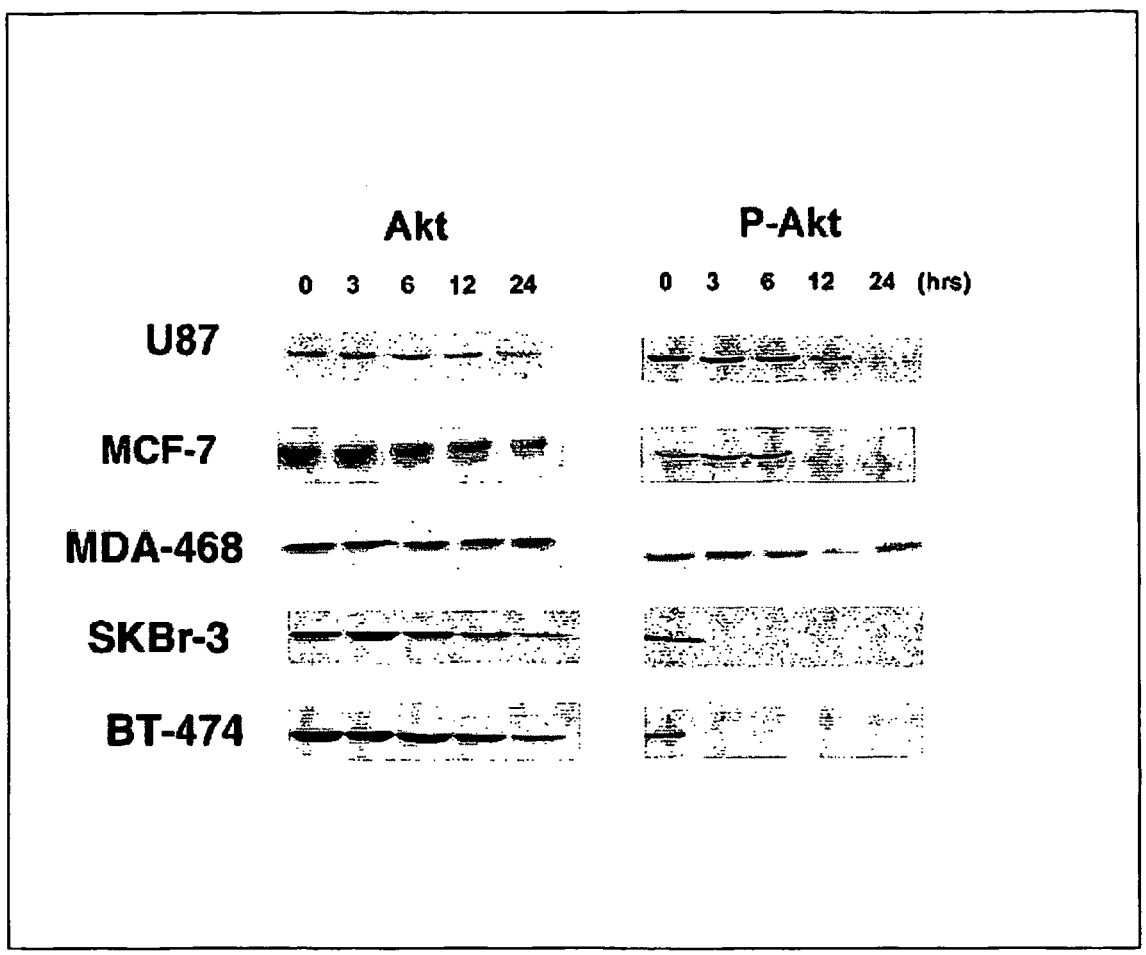
FIG. 4 shows the changes in protein levels and phosphorylation status of AKT in a panel of breast cancer cell lines after treatment with 1 uM CNF-101 (17-AAG) (17-AAG) in vitro.

Effect of CNF-101 (17-AAG) on Levels of AKT and Phosphorylated AKT in a Panel of Human Cell Lines FIG. 4 shows the changes in protein levels and phosphorylation status of AKT in a panel of breast cancer cell lines after treatment with 1 uM CNF-101 (17-AAG) in vitro. Cells were treated with 1 uM CNF-101 (17-AAG) for 24 hrs, washed, harvested and lysed in NP-40. Lysates were resolved by SDS-PAGE, transferred onto Immobilon PVDF membranes, blocked in 5% nonfat milk and probed with antibodies to AKT or tyrosine phosphorylated AKT (phospho-AKT) from Upstate. Following incubation with HRP-conjugated secondary antibodies, proteins were detected using chemiluminescnce (Amersham). AKT is a key kinase in tumor cells. The protein itself is not a HSP90 client, so treatment with CNF-101 (17-AAG) does not cause significant loss of the protein. However, because the essential upstream regulator of the AKT pathway in breast cancer (i.e. HER-2) is degraded, the signals necessary for AKT phosphorylation (and hence activity of the protein) are lost, so phospho-AKT disappears from the treated cells. This experiment demonstrates that CNF-101-induced degradation of HER-2 causes loss of AKT activity in multiple cell lines, but that those lines with high HER-2 (BT-474, SKBR-3) display a much more rapid and complete loss of AKT activity than do those lines with low HER-2 expression (U87, MCF-7, MDA-468)

EXAMPLE 5

Studies on Breast Carcinoma Xenografts

Figure 5:
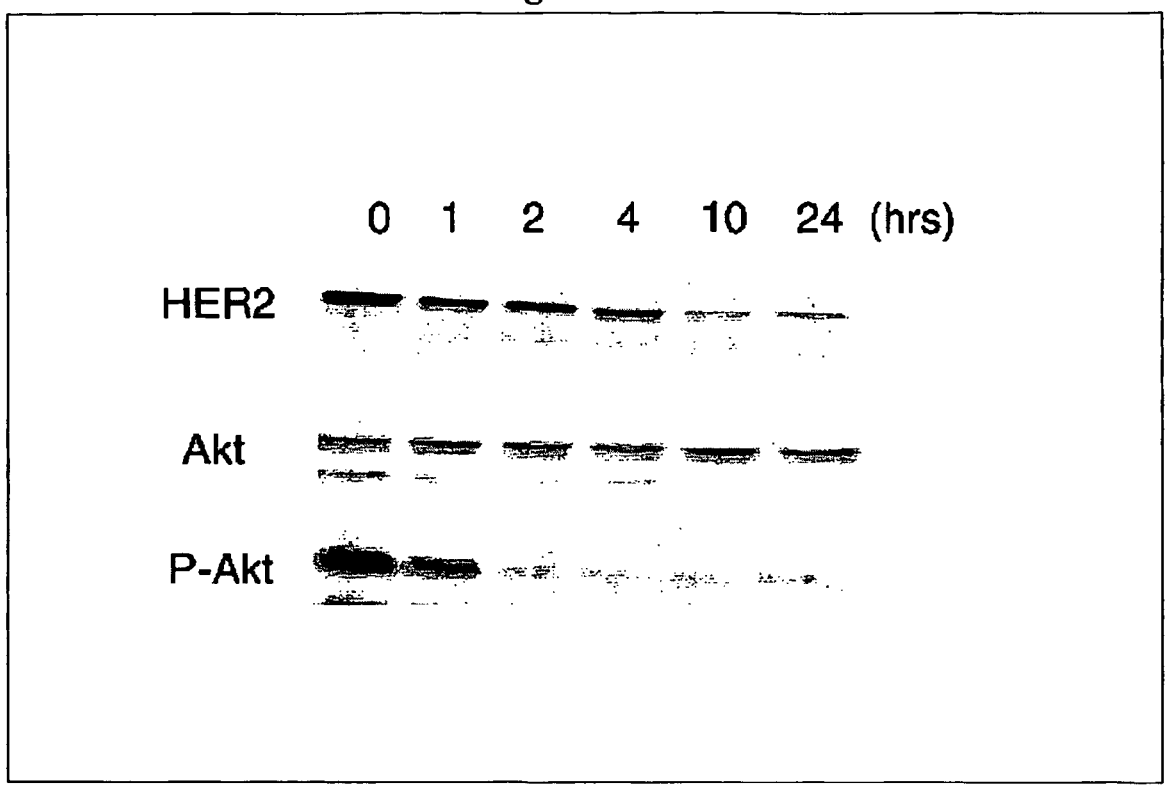
FIG. 5 shows the changes in levels of a HSP90 client protein (HER-2) and changes in protein levels and phosphorylation status of the downstream target protein AKT in HER-2+++ breast carcinoma xenografts at various times after treatment with CNF-101 (17-AAG) (17-AAG) in vivo.

FIG. 5 shows the changes in levels of a HSP90 client protein (HER-2) and changes in protein levels and phosphorylation status of the downstream target protein AKT in HER-2+++ breast carcinoma xenografts at various times after treatment with CNF-101 (7-AAG) in vivo. BT-474 breast tumor cells were implanted subcutaneously on the flank of Swiss nu/nu mice and allowed to become established to a diameter of 5 mm. Animals were treated intraperitoneally with optimal doses of CNF-101 (17-AAG) and tumors removed at the indicated times thereafter. Tumor tissue was snap-frozen at the time of removal. For analysis, tissues were rapidly thawed, lysed and assaysed for HER-2, AKT and phospho-AKT by Western blotting. This experiment demonstrates that the CNF-101-induced degradation of HER-2 and loss of AKT activity is not merely an in vitro phenomenon, but that the drug can induce these key mechanism-based changes in a whole animal setting with the same potency and kinetics.

To summarize Examples 2-5, addition of CNF-101 (17-AAG) to cultured cells results in antiproliferative effects that are strongest in cells that overexpress HER-2. For example, in cell lines that express different amounts of HER-2 (BT-174; SKBR-3>SK– OV-3>MCF-HER-2>MDA-435>MCF-7; MDA-231; MDA-468>T47-D), cells expressing higher amounts of HER-2 were more sensitive to the HSP90 inhibitor, CNF-101 (17-AAG), than cells expressing low amounts of HER-2 (See FIG. 1).

Western blot analysis of protein expression in cells overexpressing HER-2 (BT-474) and in cells which are HER-2 low (e.g., MCF-7) after treatment with either 50 nM or 500 nM CNF-101 (17-AAG) at 0, 4, 12, and 24 hours indicated that treatment of cells overexpressing HER-2 resulted in a decrease in cyclin-D1 and cyclin-D3 protein expression (FIG. 2). This decrease was not seen when HER-2 negative cells were treated with CNF-101 (17-AAG), whereas the drug did cause degradation of the HSP90 client protein Raf-1 in both cell types (FIG. 2).

Further, treatment of cells which overexpress HER-2 with CNF-101 (17-AAG) resulted in rapid loss of AKT kinase activity and amount of phosphorylated (=active) AKT (FIGS. 3 and 4). This rapid loss of AKT activity and phosphorylated AKT was not seen in cells which express low amounts of HER-2 (FIGS. 3 and 4). The effect of CNF-101 on the phosphorylation level and activity of AKT correlates with the data shown in FIG. 1, which shows that cells which overexpress HER-2 are more sensitive to HSP90 inhibitors than cells which express low levels of HER-2. Similarly, those cells which express the highest amounts of HER-2 showed the most rapid loss of AKT phosphorylation, suggesting that the inhibition of cell proliferation shown in FIG. 1 is due to down-regulation of AKT activity, and that the loss of AKT activity is itself induced by the degradation of HER-2.

Analysis of protein expression and AKT phosphorylation levels of of BT-474 Xenografts treated with 50 mg/kg CNF-101 (17-AAG), showed that HER-2 protein levels declined, AKT protein levels remained constant, but that the amount of phosphorylated ("active") AKT protein declined rapidly (FIG. 5). These data demonstrate that the effects of CNF-101 (17-AAG) shown in vitro are also valid in vivo.

Example 6

Formulation and Administration of Pharmaceutical Compositions

Geldanamycin may be prepared according to U.S. Pat. No. 3,595,955 using the subculture of *Streptomyces hygroscopicus* that is on deposit with the U.S. Department of Agriculture, Northern Utilization and Research Division, Agricultural Research, Peoria, Ill., USA, accession number NRRL 3602. Numerous derivatives of this compound may be fashioned as specified in U.S. Pat. Nos. 4,261,989, 5,387,584, and 5,932,566, according to standard techniques.

Those of ordinary skill in the art are familiar with formulation and administration techniques that can be employed in use of the invention, e.g., as discussed in Goodman and Gilman's, The Pharmacological Basis of Therapeutics, current edition; Pergamon Press; and Remington's Pharmaceutical Sciences (current edition.) Mack Publishing Co., Easton, Pa.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intraventous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g, out of a porous, non-porous, or gelatinous material, including membranes, such as sialastic membranes, or fibers. The administration can also be by direct injection at the site (or former site) of a tumor or neoplastic or pre-neoplastic tissue.

Still further, the therapeutic or pharmaceutical composition can be delivered in a vesicle, e.g., a liposome (see, for example, Langer, 1990, Science, 249:1527-1533; Treat et al., 1989, *Liposomes in the Therapy of Infectious Disease and Cancer*, Lopez-Bernstein and Fidler (eds.), Liss, N.Y., pp. 353-365).

The pharmaceutical compositions used in the methods of the present invention can be delivered in a controlled release system. In one embodiment, a pump may be used (see, Sefton, 1987, CRC Crit. Ref. Biomed. Eng. 14:201; Buchwald et al., 1980, *Surgery*, 88:507; Saudek et al., 1989, *N. Engl. J. Med.*, 321:574). Additionally, a controlled release system can be placed in proximity of the therapeutic target. (see, Goodson, 1984, *Medical Applications of Controlled Release*, Vol. 2, pp. 115-138).

The pharmaceutical compositions used in the methods of the instant invention can contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropyl-cellulose, or a time delay material such as ethyl cellulose, or cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The HSP90 inhibitors used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an HSP90 inhibitor can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods and compounds of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of antineoplastic agents, which can be used in combination with the methods of the present invention include, in general, alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors.

Example classes of antineoplastic agents include, for example, the anthracycline family of drugs, the vinca drugs, the mitomycins, the bleomycins, the cytotoxic nucleosides, the epothilones, discodermolide, the pteridine family of drugs, diynenes and the podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a HSP90 inhibitor used in the methods of the present invention is administered into a human subject, the daily dosage will normally be determined by the prescribing physician with the dosage generally varying according to the age, weight, and response of the individual patient, as well as the severity of the patient's symptoms.

In one exemplary application, a suitable amount of a HSP90 inhibitor is administered to a mammal undergoing treatment for cancer, for example, breast cancer. Administration occurs in an amount of each type of inhibitor of between about 0.1 mg/kg of body weight to about 60 mg/kg of body weight per day, preferably of between 0.5 mg/kg of body weight to about 40 mg/kg of body weight per day. A particular therapeutic dosage that comprises the instant composition includes from about 0.01 mg to about 1000 mg of a HSP90 inhibitor. Preferably, the dosage comprises from about 1 mg to about 1000 mg of a HSP90 inhibitor.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, preferably from about 1 mg to 300 mg, more preferably 10 mg to 200 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the HSP90 inhibitors used in the methods of the present invention and if applicable other chemotherapeutic agents and/or radiation therapy will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the HSP90 inhibitor and the chemotherapeutic agent do not have to be administered in the same pharmaceutical composition, and may, because of different physical and chemical characteristics, have to be administered by different routes. For example, the HSP90 inhibitor may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of HSP90 inhibitor, and chemotherapeutic agent and/or radiation will depend upon the diagnosis of the attending physicians and their judgment of the condition of the patient and the appropriate treatment protocol.

The HSP90 inhibitor, and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the HSP90 inhibitor.

If the HSP90 inhibitor, and the chemotherapeutic agent and/or radiation are not administered simultaneously or essentially simultaneously, then the initial order of administration of the HSP90 inhibitor, and the chemotherapeutic agent and/or radiation, may not be important. Thus, the HSP90 inhibitor may be administered first followed by the administration of the chemotherapeutic agent and/or radiation; or the chemotherapeutic agent and/or radiation may be administered first followed by the administration of the HSP90 inhibitor. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the HSP90 inhibitor followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent-i.e., HSP90 inhibitor, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The foregoing examples are not limiting and are merely representative of various aspects and features of the present invention. All documents cited are indicative of the levels of skill in the art to which the invention pertains. The disclosure of each document is incorporated by reference herein to the same extent as if each had been incorporated by reference in its entirety individually, although none of the documents is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

It will be readily apparent to one skilled in the art that varying substitutions and modifications may be made to the invention without departing from the scope and spirit of the invention. Thus, such additional embodiments are within the scope of the invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention in the use of such teims and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group, and exclusions of individual members as appropriate.

Other embodiments are within the following claims.

We claim:

1. A method of treating a patient having breast cancer characterized by breast cancer cells that have elevated levels of HER-2 expression as compared to non-cancerous cells of the same type, comprising:

providing breast cancer cells from said patient;

testing said provided cells for one or more of the gene copy number of HER-2 the amount of HER-2 mRNA, or the amount of HER-2 protein as an indication of the level of HER-2 expression; and if said level of HER-2 expression is elevated as compared to non-cancerous cells of the same type, administering to said patient a pharmaceutically effective amount of an HSP90 inhibitor, wherein said HSP90 inhibitor has an $IC_{50}$ at least two-fold lower for said provided cells in said patient having elevated Her-2 than for cells that do not have elevated Her-2 and the administered amount is correspondingly lower than the amount that would be required for cells that do not have elevated Her-2, and wherein said method of treating a patient further comprises testing to monitor therapeutic effect after said administration by measuring a molecular marker indicative of the level of HER-2 wherein said inhibitor consists essentially of an ansamycin that binds into the ATP-binding site of a HSP90.

2. The method of claim 1 wherein said testing comprises using nucleic acid hybridization or PCR to determine the level of HER-2 messenger RNA.

3. The method of claim 1 wherein said testing comprises the use of antibodies to determine the level of HER-2.

4. The method of claim 1 wherein said testing is done ex vivo.

5. The method of claim 1 wherein said administering is intralesional.

6. The method of claim 1 wherein said administering is parenteral.

7. The method of claim 1 wherein said HSP90 inhibitor has an $IC_{50}$ at least five-fold lower for said cells in said patient having elevated Her-2 than for cells that do not have elevated Her-2.

8. The method of claim 1 wherein said HSP90 inhibitor has an $IC_{50}$ at least ten-fold lower for said cells in said patient having elevated Her-2 than for cells that do not have elevated Her-2.

9. The method of claim 1 further comprising testing cells of said patient for sensitivity to HSP90 inhibitors prior to administration of said HSP90 inhibitor.

10. The method of claim 1 wherein said testing comprises the use of one or more standards.

11. The method of claim 1 wherein said inhibitor exhibits an $IC_{50}$ of about 100 nM or less in said cells having elevated Her-2.

12. The method of claim 1 wherein said inhibitor exhibits an $IC_{50}$ of about 75 nM or less in said cells having elevated Her-2.

13. The method of claim 1 wherein said inhibitor exhibits an $IC_{50}$ of about 50 nM or less in said cells having elevated Her-2.

14. The method of claim 1 wherein said inhibitor exhibits an $IC_{50}$ of about 25 nM or less in said cells having elevated Her-2.

15. The method of claim 1 wherein said inhibitor exhibits an $IC_{50}$ of about 10 nM or less in said cancerous cells.

16. The method of claim 1 wherein said inhibitor exhibits an $IC_{50}$ of about 5 nM or less in said cells having elevated Her-2.

17. A method of treating a patient having breast cancer characterized by breast cancer cells that have elevated levels of HER-2 expression as compared to non-cancerous cells of the same type, comprising:
providing breast cancer cells from said patient;
testing said provided cells for one or more of the gene copy number of HER-2 the amount of HER-2 mRNA, or the amount of HER-2 protein as an indication of the level of HER-2 expression; and if said level of HER-2 expression is elevated as compared to non-cancerous cells of the same type, administering to said patient a pharmaceutically effective amount of an HSP90 inhibitor, wherein said HSP90 inhibitor has an $IC_{50}$ at least two-fold lower for said provided cells in said patient having elevated Her-2 than for cells that do not have elevated Her-2 and the administered amount is correspondingly lower than the amount that would be required for cells that do not have elevated Her-2, and wherein said method of treating a patient further comprises testing to monitor therapeutic effect after said administration by measuring a molecular marker indicative of the level of HER-2 wherein said inhibitor is an ansamycin that binds into the ATP-binding site of a HSP90, wherein said molecular marker is selected from one or more of the group consisting of a cyclin, and phosphorylated AKT.

18. The method of claim 17 wherein said molecular marker is a cyclin selected from the group consisting of D1 and D3.

19. The method of claim 1, wherein said cells that do not have elevated Her-2 are from said patient.

20. The method of claim 1, wherein said $IC_{50}$ value is calculated using one or more standards.

21. The method of claim 1 wherein said elevated level is at least two-fold greater for said cells in said patient having elevated Her-2 than for cells that do not have elevated Her-2.

22. The method of claim 1 wherein said elevated level is at least three-fold greater for said cells in said patient having elevated Her-2 than for cells that do not have elevated Her-2.

23. The method of claim 1 wherein said elevated level is at least five-fold greater for said cells in said patient having elevated Her-2 than for cells that do not have elevated Her-2.

24. The method of claim 1 wherein said elevated level is at least ten-fold greater for said cells in said patient having elevated Her-2 than for cells that do not have elevated Her-2.

25. The method of claim 1 wherein said elevated level is at least twenty five-fold for said cells in said patient having elevated Her-2 than for cells that do not have elevated Her-2.

26. The method of claim 1, wherein said ansamycin is selected from the group consisting of geldanamycin, 17-AAG, herbimycin A, and macbecin.

27. The method of claim 1, wherein said inhibitor is 17-AAG.

28. A method of treating a patient having breast cancer characterized by breast cancer cells that have elevated levels of HER-2 expression as compared to non-cancerous cells of the same type, comprising:
providing breast cancer cells from said patient;
testing said provided cells for the gene copy number of HER-2; and if said gene copy number is elevated as compared to non-cancerous cells of the same type, administering to said patient a pharmaceutically effective amount of an HSP90 inhibitor, wherein said HSP90 inhibitor has an $IC_{50}$ at least two-fold lower for said provided cells in said patient having elevated Her-2 than for cells that do not have elevated Her-2 and the administered amount is correspondingly lower than the amount that would be required for cells that do not have elevated Her-2, and wherein said method of treating a patient further comprises testing to monitor therapeutic effect after said administration by measuring a molecular marker indicative of the level of HER-2 wherein said inhibitor consists essentially of an ansamycin that binds into the ATP-binding site of a HSP90.

29. The method of claim 1, wherein said testing to determine the HER-2 gene copy number is done using a Southern blot technique.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: primer for amplification of HER-2

<400> SEQUENCE: 1
tctggacgtg ccagtgtgaa                                            20

<210> SEQ ID NO 2
<211> LENGTH: 20
<212> TYPE: DNA
<213> ORGANISM: Artificial
<220> FEATURE:
<223> OTHER INFORMATION: primer for amplification of HER-2

<400> SEQUENCE: 2
tgctccctga ggacacatca                                            20

<210> SEQ ID NO 3
<211> LENGTH: 24
<212> TYPE: DNA
<213> ORGANISM: Artificial
<220> FEATURE:
<223> OTHER INFORMATION: hybridization probe for HER-2

<400> SEQUENCE: 3
cagaaggcca agtccgcaga agcc                                       24
```